United States Patent [19]

Krull et al.

[11] Patent Number: 4,661,235
[45] Date of Patent: Apr. 28, 1987

[54] CHEMO-RECEPTIVE LIPID BASED MEMBRANE TRANSDUCERS

[76] Inventors: Ulrich J. Krull, 151 LaRose Ave., Weston, Ontario, Canada, M9P 1B3; Michael Thompson, 1824 Delaney Dr., Mississanga, Ontario, Canada, L5J 3L1

[21] Appl. No.: 637,565

[22] Filed: Aug. 3, 1984

[51] Int. Cl.[4] ............................................. G01N 27/30
[52] U.S. Cl. .................................... 204/414; 204/1 T; 204/403; 204/415; 204/418; 435/4; 435/7; 435/11; 435/291; 435/817
[58] Field of Search ............... 204/415, 418, 403, 1 N, 204/414, 1 T, 1 A; 435/817, 291, 4, 7, 11

[56] References Cited

U.S. PATENT DOCUMENTS 3,607,700  9/1971  Tosteson ........................ 204/1 T X
4,490,216  12/1984  McConnell ........................ 204/1 T

OTHER PUBLICATIONS

Ulrich Jörg Krull, "Lipid Membrane Dipole Pertubation and Chemoreception as Models for a Selective Chemical Sensor", (1983).
H. Ti Tien, "Bilayer Lipid Membranes—Theory and Practice", pp. 117–137, (1974).
Krull et al, Abstract 11—1, 67th Annual CIC Conference, (Jun. 1984).
Thompson et al, *Analytica Chimica Acta*, 117: 121–132, 133–145, (1980).
Albrecht et al, *Biochimica et Biophysica Acta*, 687: 165–169, (1982).
Kuhn, *Thin Solid Films*, 99: 1–16, (1983).
Demel et al, *Biochimica et Biophysica Acta*, 255: 311–320, (1972).
Demel et al, *Biochimica et Biophysica Acta*, 255: 321–330, (1972).
De Kruyff et al, *Biochimica et Biophysica Acta*, 255: 331–347, (1972).
Gallay et al, *FEBS LETTERS*, 143(1): 133–136, (1982).
Thompson and Krull, *Analytica Chimica Acta*, 141: 33–47, 49–56 (1982).
Thompson and Krull, *Analytica Chimica Acta*, 142: 207–216, (1982).
Thompson et al, *Biochemical and Biophysical Research Communications*, 110(1): 300–304, (Jan. 1983).
Thompson and Krull, *Analytica Chimica Acta*, 147: 1–21, (1983).
Thompson, Krull and Bendell—Young, Proceedings International Symposium in Chemical Sensors, pp. 576–581, (Sep. 1983).
Thompson, Krull and Bendell—Young, *Talanta*, 30(12): 919–924, (1983).
Thompson, Krull and Arya, "Towards an Electrochemically—Based Chemoreceptor for Trace Atmospheric Organics," presented at Technology Transfer Conference No. 4, University of Waterloo (Mar. 1984).
Winnsborrow, Krull and Thompson, Abstract IV—1, and King, Krull and Thompson, Abstract IV—3, Student Chemistry Conference, University of Waterloo (Mar. '84).
Krull, Thompson and Arya, *Talanta*, 31(7): 489–495, (Jul. 1984).

*Primary Examiner*—G. L. Kaplan
*Attorney, Agent, or Firm*—Lyon & Lyon

[57] ABSTRACT

A lipid membrane is used as a chemo-receptive transducer for quantitative and semi-quantitative analysis of chemical test species in an electrolyte. The lipid membrane is contacted with an electrolyte containing the test species, and an electrical potential difference is applied across the membrane. From measurements of the trans-membrane ion current variation due to the presence of the test species, a quantitative analysis of the test species may be conducted, on a highly selective basis. Receptors showing a high degree of selectivity towards the test species are included in the membrane.

18 Claims, 11 Drawing Figures

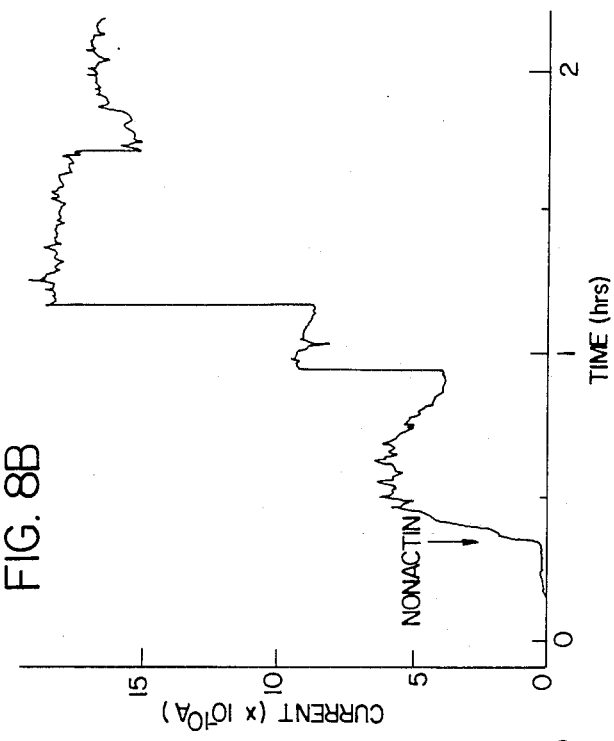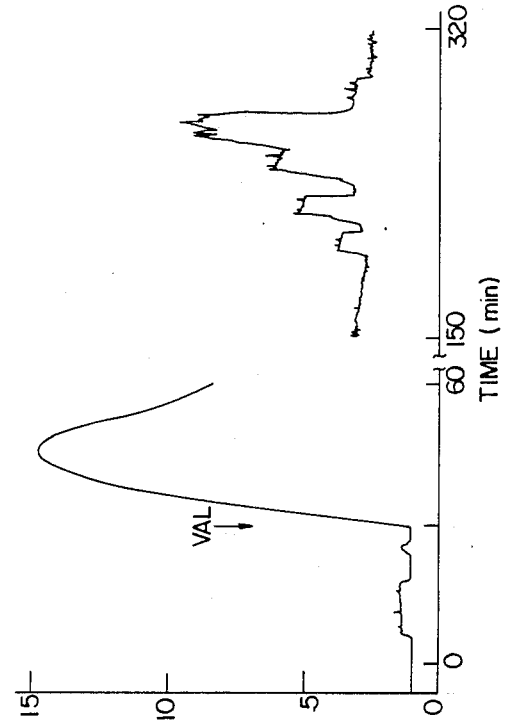

CHEMO-RECEPTIVE LIPID BASED MEMBRANE TRANSDUCERS

This invention relates to chemical analysis methods, and more particularly to determination of concentrations of chemical species in aqueous electrolyte, by use of ion permeable lipid membranes.

Ion permeable lipid membranes are well-known in the biochemical and chemical fields. They were originally developed to simulate artificially the complex biological membranes such as double unit cell membranes and internal cell structures, which are basic elements of life. Commonly, they are bilayer lipid membranes (BLM), consisting of two adjacent lipid monolayers oriented in a symmetrical but opposing manner, of overall thickness about 6-8 nm. Chemically, the structure has a central non-polar hydrocarbon region, bounded on both sides with polar sheets of lipid headgroups. They are formed and sustained in supporting aqueous electrolyte, the lipid headgroups being hydrated thereby. Hydrophobic attraction of the non-polar regions in water holds the membrane structure together. They can be chemically modified to incorporate stabilizers therein. Monolayer lipid membranes are also known, but are less commonly prepared and used—they tend to assume a spherical configuration in water, or coat other substrates at the substrate-water inferface. The preparation and properties of bilayer lipid membranes are fully described in textbooks and literature articles—see for example "Bilayer Lipid Membranes (BLM) - Theory and Practice", H. Ti Tien, published by Marcel Dekker, Inc., New York, 1974.

The application of a direct electric potential across a bilayer lipid membrane structure results in the passage of a small but finite ion current through the membrane. A typical current-voltage curve for a stable BLM has ohmic response over a range of approximately $-60$ to $+60$ mV with the current usually being of the order of $10^{-9}$ A/cm$^2$ at 50 mV.

The present invention is based upon the fact that incorporation of and membrane interaction with molecules or complexes which alter the standing transmembrane ion flux results in the production of an analytical signal. A membrane-bound receptor/stimulant interaction which translates the binding event into a transmembrane ionic flux, i.e. alters the conductance of the membrane, is utilized as a sensitive and selective electrochemical sensor of the stimulant.

The present invention senses the presence and indicates the concentrations of chemical species under test, by measuring the changes in the parameters of an ion-permeable lipid membrane immersed in an aqueous electrolyte, caused by the presence of the chemical species. More particularly, the alteration of the membrane parameters caused by the chemical species (stimulant) changes the conductivity of the membrane to ions. The changing conductivity can be directly measured, to determine the concentration of the chemical species, by application of a driving force for transmembrane ion movement. The chemical species under test undergoes selective chemical complexation with a complexing agent (receptor) located on, or in, the membrane, which causes the change in conductivity of the membrane to ions. Thus the method of the present invention does not rely on complexation reaction evolution, measurements of concentration of product formation or similar measurements of secondary products of a selective reaction. It employs the primary complexation event for signal generation, with consequent benefits of increased sensitivity, fast response time, lower detection limits, small size and potentially increased functional lifetime.

In the accompanying drawings:

FIGS. 7 and 8a and 8b are similar graphs, from Example 6;

The present invention utilizes the changes in ion permeability/conductivity of an ion permeable lipid membrane, caused by complexation with the test species or stimulant. For use in the process of the present invention, the BLM should preferably be prepared from a lipid which is naturally occurring, produces a stable membrane, and gives a membrane having no net charge at neutral pH of the electrolyte in which it is immersed.

Suitable lipids for formation of a BLM for use in the present invention include phospholipids such as phosphatidic acid, diphosphatidyl glycerol, phosphatidyl glycerol, phosphatidyl choline, phosphatidyl ethanolamine, phosphatidyl serine, phosphatidyl inositol, phosphatidyl compounds with acyl chains such as mono- or di- palmitoyl, mono- or di- myristoyl, mono- or di- phytanoyl, mono- or di- stearoyl, and mono- or dioleoyl; syphingolipids such as ceramides and cerebrosides; glycolipids such as mono- or di- galactosyl diglyceride; and other lipids or lipid analogues such as glycerol mono-oleate, oxidized cholesterol and egg-phosphatidyl choline.

The hydrophobic chain portion of the compounds should be chosen, as regards its chemical composition and its length, with a view to obtaining suitable membrane stability and suitable thickness of hydrophobic zone thereof. Since, in the process of the invention, the hydrophobic zone acts as one barrier or modulator of ion flow, i.e. conductivity, the appropriate thickness of the zone will depend to some extent upon the minimum current to be measured in the analytical process. Normally the zone has a thickness of from about 4.0 nm to about 7.0 nm. This is preferably provided by acyl chains of length C14-C24 on the lipid headgroups, e.g. egg phosphatidyl choline, which has a chain length of about C18.

Figure 1:
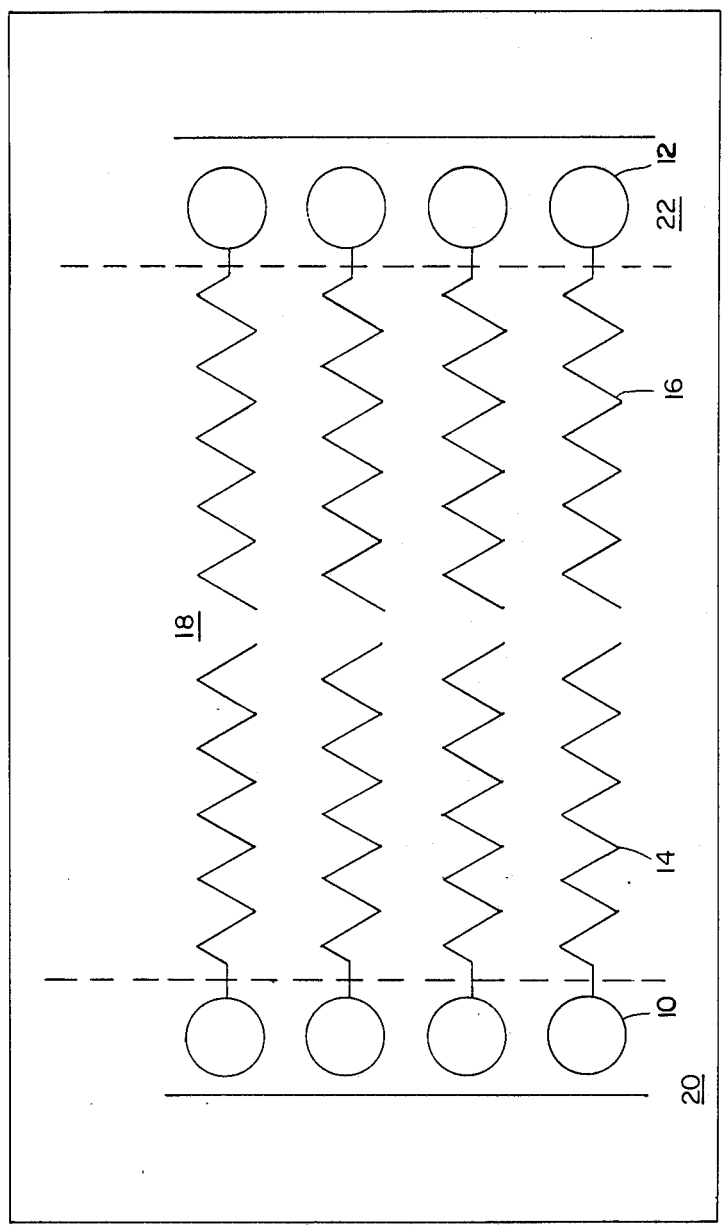
FIG. 1 is a diagrammatic cross-sectional representation of a standard bilayer lipid membrane (BLM)

With reference to FIG. 1 of the accompanying drawings, a conventional bilayer lipid membrane comprises molecules having polar, hydrophilic lipid heads 10, 12 and hydrophobic organic tails 14, 16. The molecules arrange themselves, in an aqueous electrolyte, in a bilayer arrangement with the hydrophobic tails adjacent to form an organic phase region 18, and the hydrophilic lipid heads separated to form two separate aqueous phase regions 20, 22. In practice the organic phase 18 acts as one barrier to passage of ions through the membrane. The conductance characteristics of the membrane can thus be varied by varying the nature and composition of organic phase 18. This can be done by chemical modification of the organic tails 14, 16 of the molecules.

For example, the incorporation of polar groups in the chains 14, 16 will lead to mutual electrostatic repulsion between the chains and cause a spreading effect to reduce the density and hence increase the permeability of the organic phase 18 to ion passage. At the same time, the presence of polar chemical groups in the organic phase 18 will create zones therein which are of low energy and through which ionic test species can move with relative ease. Moreover, the polar groups in the organic phase 18 may act as binding sites, to attract and hold ionic test species in the organic phase, thereby increasing its overall polarity and hence increasing its conductance towards ion flow. This increased conductance has the effect of increasing the sensitivity of the membrane towards ion concentration measurements.

One can also adjust the ion permeability and hence the conductance of the BLM by controlling the "packing density" of the lipid head groups 10, 12. This may be done by incorporating into the BLM modifying membrane structural agents whose molecules will interpose between the individual head groups 10, 12, such as steroids, for example cholesterol. Such substances have molecular chains compatible with the organic phase 18 of the BLM so that they align therewith, with head groups interposed between the BLM head groups 10, 12. When phosphatidyl choline is chosen for use as the BLM, various oxidised cholesterol species are preferred for incorporation therein for packing density reduction of the lipid head groups. The incorporation of the stabilizer may be accomplished by including it in the ingredients from which the BLM is prepared. The hydrophobic chains 14, 16 of phosphatidyl choline may contain carbon-carbon unsaturation, which provides sites for chemical modification to introduce polar groups therein. By a combination of these techniques, one can adjust and control the BLM permeability and ion conductance, to make the effects of the test species (stimulant)-receptor reaction on the BLM ion conductance as marked as possible. The BLM conductance may be adjusted to different levels depending upon the chosen stimulatant-receptor pair.

In cases where an organic compound is the test species to be measured, the BLM used in the present invention contains a receptor, for reaction with the stimulant (test species) on or in the BLM to change its ion permeability. The receptor may be physically embedded or chemically bound in the membrane. For use in a permanent analytical system or instrument, the receptor should not be easily extractable therefrom. The choice of appropriate receptor makes the process highly selective for analysis of the specific chosen stimulant. Preferably the chosen receptor is one which does not react to any appreciable extent with the ions of the electrolyte in which the analysis is being conducted, and whose flow through the membrane is to be measured as membrane conductance. In other words, the receptor should have a selectivity towards the organic stimulant. The receptor may be incorporated into the BLM at the time the BLM is prepared, by including the receptor in the ingredients for forming the BLM in the electrolyte, or by absorption into the membrane from aqueous solution. Commonly, the receptor is a natural product, especially when biochemical or biological stimulants are to be measured.

When an inorganic stimulant is to be measured, the BLM may be made selectively permeable to passage therethrough of the inorganic stimulant, suitably in complexed and/or ionic form, as discussed below. In such cases, the conductance of the membrane towards the actual stimulant under test, or a complexed ionic form thereof, is measured in the process of the present invention.

Figure 2:
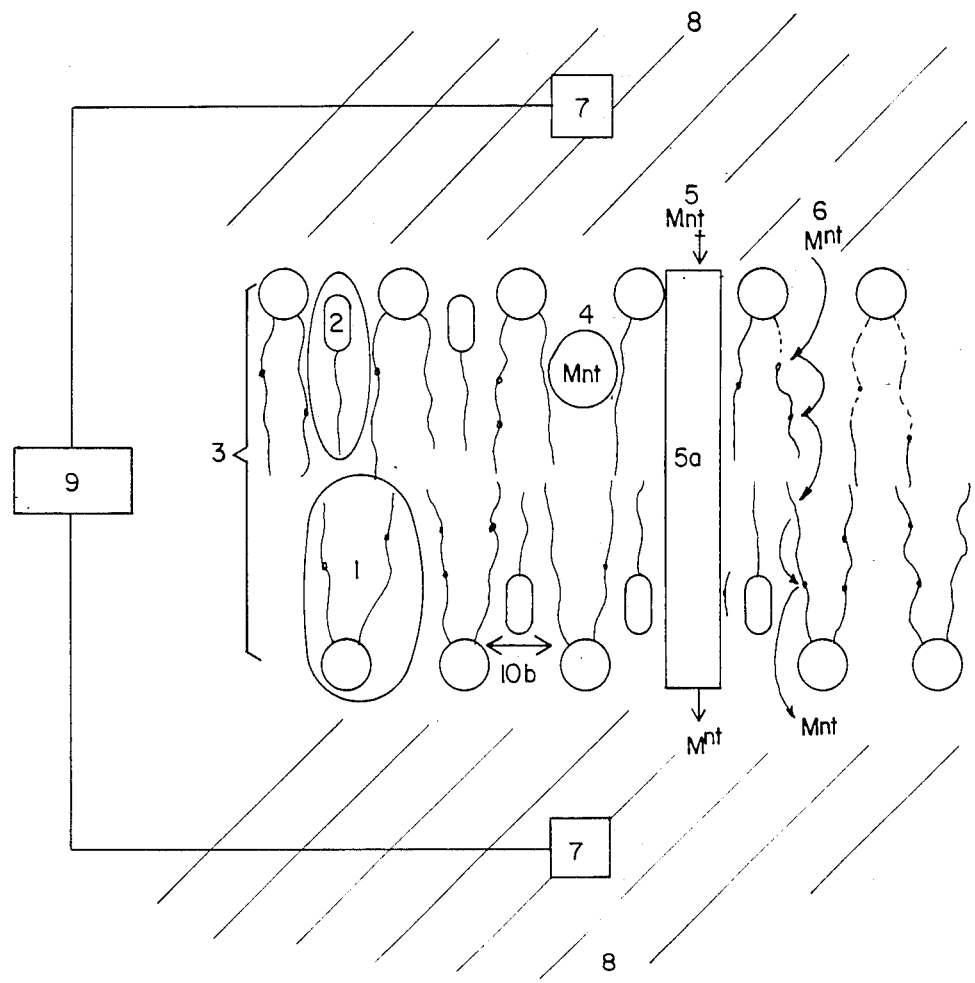
FIG. 2 is a diagrammatic illustration of various transport mechanisms of ions through a BLM in processes according to the invention.

FIG. 2 of the accompanying drawings illustrates diagrammatically the mechanisms by which an ionic species $M^{n+}$ may move through a BLM under applied electric potential. The BLM 3 is immersed in electrolyte 8 containing inorganic ions $M^{n+}$. In addition to lipid molecules 1 as previously described the BLM 3 includes a modifying membrane structural agent 2 such as a sterol, surfactant or polymer to alter the density and permeability of the head group layer. Electrodes 7 for electrochemical measurements, such as Ag/AgCl reference electrodes, are placed in the electrolyte 8 on either side of the BLM 3. An external circuit 9 provides the ion driving force and measures the electrical characteristics of the membrane, such as the ion current, resistance or capacitance.

In the case of ionic species $M^{n+}$ represented at 4, this is itself the stimulant whose concentration is to be measured. It is conducted through the membrane 3 by complexation to form a hydrophobic ion. In this mechanism, ion $M^{n+}$ forms a complex with a hydrophobic species, so that the polar ion $M^{n+}$ is shielded from the non-polar internal membrane structure. This results in a lowering of the Born energy requirement for ion injection into the hydrophobic zone. The complex formed is a hydrophobic ion, and diffusion through the membrane is greatly influenced by the surface or dipolar potentials and membrane fluidity Examples of suitable complexing reagents include ion-complexing antibiotics such as valinomycin and nonactin, and crown ethers. By choice of a complexing agent which is extremely selective to a chosen inorganic ion $M^{n+}$, the concentration of the chosen inorganic ion $M^{n+}$ in the electrolyte 8 can be determined from the change in conductivity of the membrane BLM sensed by the ion flow. The receptor or complexing agent should be preferably at least $10^3$ fold more selective to the ion of interest than to the background electrolyte, the difference in selectivity determining ion concentration detection limits. The complexing agent can be provided externally of the membrane or can be included in the ingredients for forming the BLM. They may be provided on the surface of the BLM, embedded therein at the inner part of the central non-polar region, or in the exterior electrolyte. In many cases they may be viewed as providing an outer organic "coating" for the inorganic ion to facilitate its transport through the non-polar, centre regions of the BLM.

Before analytical measurements are undertaken, the system is calibrated by measurements of membrane conductance in the presence of known amounts of ionic species $M^{n+}$ and the fixed amount of complexing agent (preferably provided in quantities which can saturate incorporation into the BLM). Ion current (inorganic or organic, cationic or anionic) of this mechanism is controlled and altered by any selective interaction modifying the inherent bilayer dipolar potential or molecular packing characteristics.

Examples of suitable ionic species and selective complexing agents therefor include potassium ion-valinomycin, and ammonium ion-nonactin. Thus, valinomycin has $10^4$ more selectivity towards $K^+$ than towards sodium ion $Na^+$. Ammonium ion-gramicidin A is another suitable selective agent and ion, but one which operates by a different mechanism, discussed below.

Ionic species $M^{n+}$ represented at 5 on FIG. 2 moves through the membrane 3 by passage through a polypeptide or protein channel 5a therein. The channel or pore 5a links the two aqueous electrolyte solution compartments. The exterior of the pore is generally hydrophobic so that incorporation in the non-polar core is facilitated. The pore interior is polar, assisting in ion transport. The pore is a chemical receptor species. Suitable examples of such ion selective receptor species are the antibiotics amphotericin B and gramicidin A, B and C. Pores so created are in many instances extremely selective to inorganic ions, resulting in an ion selective membrane, suitable for use in measuring concentration of inorganic, ionic stimulants according to the present invention, by the direct passage thereof, through the BLM as ion current.

An example of suitable ionic species and selective pores therefor include the aforementioned ammonium ion-gramicidin A. In the latter pore systems, an organic selective chemical receptor species may initially be associated with the protein or polypeptide pore incorporated in the BLM at the BLM surface. When the organic receptor binds to the test species (stimulant) and under the influence of the applied electrostatic field, it changes the conformation or electrostatics of the pore and opens up an ion selective channel flow route as it does so, to allow subsequent ion flow. Hence the stimulant-receptor reaction activates the function of the pore and changes the ion flow characteristics of the BLM. Specific examples of chemical species operating according to this "gating" mechanism include certain enzyme-substrate reactions such as acetylcholinesterase-acetylcholine; antibody-antigen complement; and auxin-receptor. Movement of conductivity changes in the membrane, from measurements of flow therethrough by a non-reactive transport ion in the electrolyte, can thus be used to measure concentration of these organic stimulants in the electrolytes. Their selective reaction with the receptor changes the membrane conductivity.

Ionic species $M^{n+}$ represented at 6 in FIG. 2 move through the BLM by a diffusion mechanism. This ion conduction is greatly influenced by molecular fluidity/packing of the non-polar core and headgroup region, and electrostatic potentials. Ion conduction is increased by increasing membrane fluidity. The introduction of polar species and groups into the hydrocarbon core assists ion conduction by offering low energy binding sites, reducing Born energy requirements, increasing fluidity and reducing packing. Thus the presence in the BLM 3 of a stabilizer substance such as an oxidized sterol, and the presence of polar groups in the lipid hydrocarbon tail chains, affects ion conductance by these mechanisms.

Specific examples of pairs of stimulants and receptors operating by this mechanism include trypsin-inhibitor; and concanavalin A-saccharide.

It will be appreciated that in any given BLM analytical process, according to this invention, only one of the previously described mechanisms is used. The choice is based on the nature of the stimulant and hence the nature of the complementarily chosen receptor. The type of mechanism which the process will follow is determined by the composition of the BLM.

Figure 3:
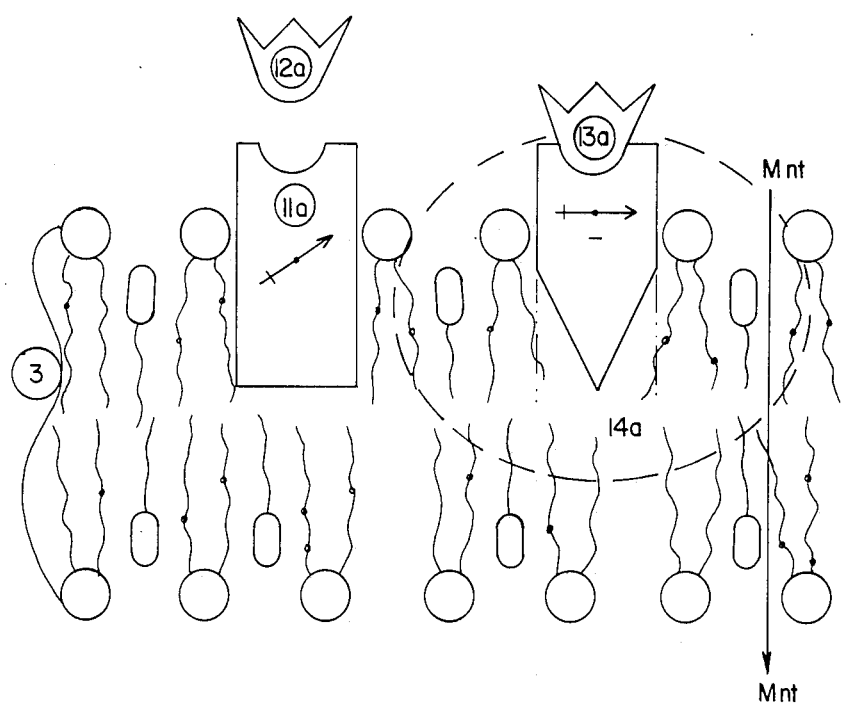
FIG. 3 is a diagrammatic illustration similar to FIG. 2 showing complexation reactions within a BLM in processes according to the present invention.

With reference to FIG. 3 of the accompanying drawings, this illustrates diagrammatically a receptor-stimulant system in a BLM for use in the present invention especially for sensing and measuring organic stimulants. The BLM 3 has embedded therein a suitable chemical receptor 11a which is selective for reaction with an organic stimulant 12a present in the electrolyte. Upon reaction of the receptor and the stimulant, a complex 13a is formed within the BLM, which upon formation significantly alters the conductance of the BLM 3, within its area of influence 14a. As a result, an ionic species $M^{n+}$ present within the electrolyte may flow through the BLM 3, through the area 14a, with different speed, energy etc. than prior to the formation of complex 13a. The resultant change in ion conductance of BLM is related to the amount of complex 13a which has been formed which is in turn a function of the concentration of stimulator 12a in the electrolyte.

The presence of dipolar species inherent in the head group zone of the bilayer (including adsorbed water) results in the development of electrostatic fields in the head group zone, arising from the net alignment of the available dipolar species. This is a static situation which partially controls the ease with which ions enter the membrane. Selective complexation processes can be arranged to perturb this static situation, such as alteration of the net lipid dipole by head group perturbation, alteration of an initial receptor dipole contribution to the electrostatic field, introduction of a dipole due to the stimulant on complexation, or introduction of dipole due to realignment of dipoles present in the receptor stimulant complex. The analytical signal from a stimulant-receptor complexation which increases membrane ion permeability by reducing molecular packing density can be amplified by combining the process with a dipolar potential reduction.

Some examples of pairs of stimulants and receptors which operate by this mechanism include concanavalin A-saccharide; concanavalin A-saccharide-nonactin.

It will be appreciated from the foregoing that, in most instances, the ion transported through the membrane to give the measure of current and conductance of the membrane is not the stimulant or test species, but is acting merely as a current indicator. A wide variety of inorganic ions can be used for this purpose, monovalent ions such as potassium ions, sodium ions etc. being preferred. In other cases, the inorganic stimulant is itself ionic, is complexed with an appropriate receptor to form an ionic complex, and is itself monitored as it transports through the membrane to give ionic current.

In conducting a process according to the present invention, the BLM is first set up in aqueous solution, and allowed to absorb the chosen stabilizers, receptors etc., by standard techniques. The receptor preferably has a suitable hydrophilic/hydrophobic balance for ease of entry into the BLM from the aqueous solution. The membrane may be produced in the electrochemical cell in which it is to be used, or made in a remote location, maintained in stable condition in aqueous electrolyte and then introduced into the analytical cell.

Figure 4:
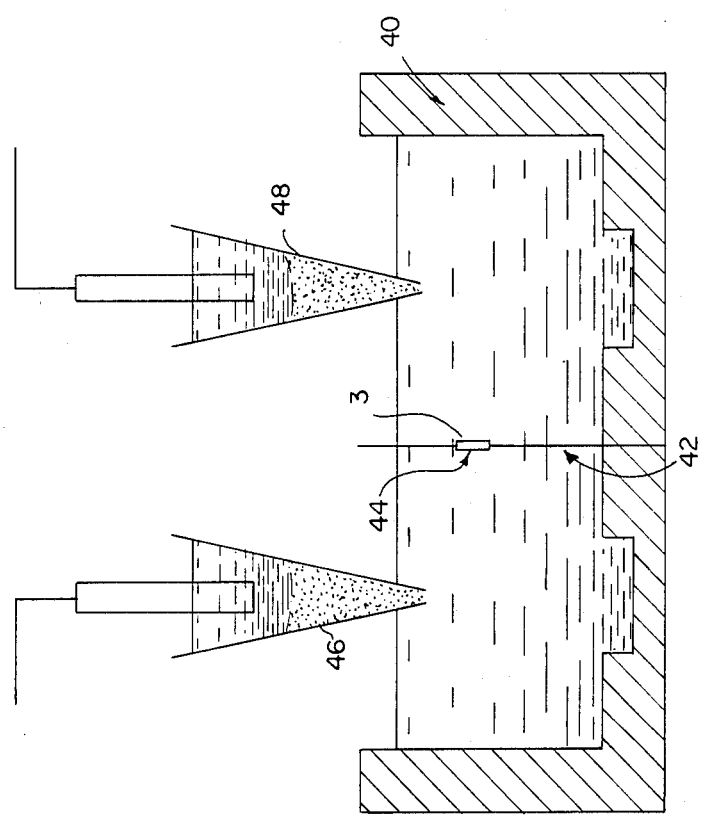
FIG. 4 is a diagrammatic cross-sectional view of an apparatus for conducting the process of the present invention, in the liquid phase.

FIG. 4 of the accompanying drawings illustrate diagrammatically a form of electrochemical cell for use in the present invention. The cell has a perspex housing 40 formed as two blocks separated by a Teflon sheet 42 of 0.1 mm thickness containing a circular aperture 44 of 1 mm diameter used to support the BLM 3. An external direct potential is applied across the membrane 3 between two agar salt bridge extended Ag/AgCl single junction reference electrodes 46, 48. The external circuitry consists of a DC power supply connected to electrode 46 and a microprocessor controlled multichannel digital electrometer for data acquisition, connected to electrode 48. An optical system consisting of a cold light halogen-quartz fiber optics illuminator and a wide angle twenty power microscope may be used to investigate and monitor BLM formation for electrochemical studies. The solution cell and sensitive electronic equipment is suitably isolated in a well grounded Faraday cage.

Figure 5:
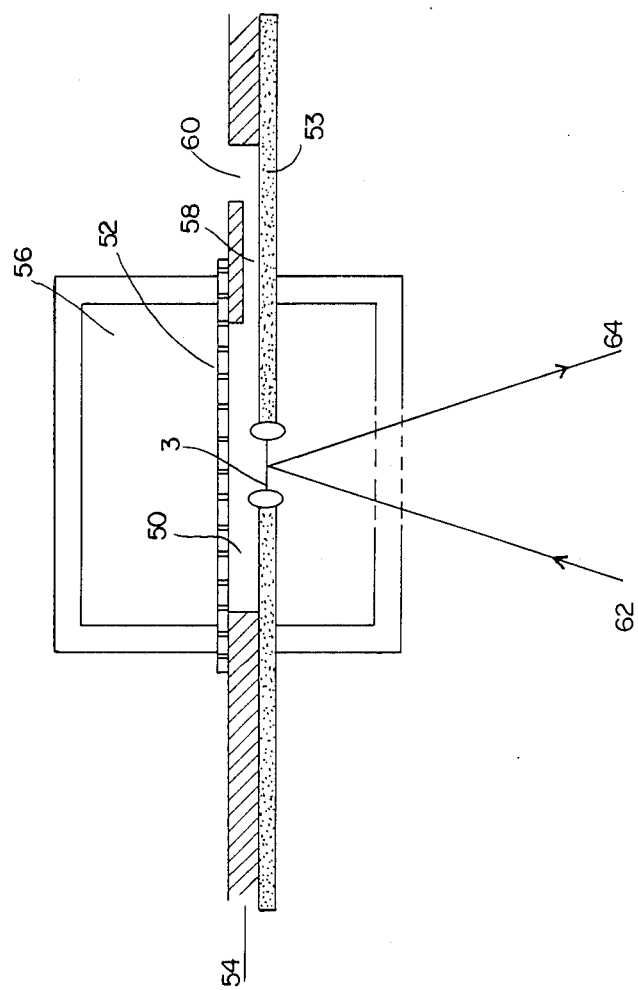
FIG. 5 is a diagrammatic cross-sectional view of an apparatus for conducting the process of the present invention for gas detection.

FIG. 5 of the accompanying drawings illustrates a gas detection device for use in the present invention, for analysis of stimulants in the gas phase. As in the case of liquid measurements, it retains the concept of two solution compartments separated by a BLM 3. A thin layer 50 of aqueous electrolyte is trapped at the upper face of membrane 3 by means of a porous Teflon semi-permeable membrane 52 (designed for use with an ammonia electrode), separated from the BLM support 53 by a perspex block 54. This allows interfacing to the gas phase in the upper compartment 56. The trapped aqueous layer 50 was connected by means of a thin channel 58 to an Ag/AgCl reference electrode 60. A light source 62 and microscope optics 64 are provided, to observe the BLM 3 under test.

Free membranes are extremely sensitive to mechanical shock, and so it is preferred to stabilize a BLM before its use in the present invention. There are several ways in which this can be done. In one method, polymers such as polyethylene or polyvinylchloride are added to the hydrocarbon solvent from which the BLM is deposited, in amounts up to about 5% w/v. The polymer incorporates into the BLM to add some structural stability thereto. In a second method, surfactants may be added, for example hexadecyltrimethylammonium bromide. These can be added for incorporation in the BLM in substantially the same manner as sterols previously discussed. A further stabilization method involves internal polymerization. In this method, the membrane internal acyl chains contain functional groups which can be covalently chemically linked, thereby causing a controlled, but permanent, density change.

A particularly preferred stabilization method, however, involves deposition of the membrane onto a support. In this method, ordered lipid membranes may be deposited on ion conductive supports, either solids or stable gel substrates, by thin film deposition methods to provide a supported membrane. In one specific method, the membrane is deposited on a hydrogel, which is physically stabilized on an electrochemical reference electrode.

In such supported membranes for use in the present invention, for added mechanical strength, the lipid headgroups of the membrane can be covalently bonded to the support, or physically absorbed on the support. In such arrangements, monolayer lipid membranes instead of bilayer lipid membranes can be prepared and used.

The invention is further described in the following non-limiting examples.

EXAMPLE 1—Formation of BLM

The BLM were formed from solutions containing n-decane (which had been purified over an alumina column and dried over molecular sieves) and lipid/cholesterol in 2%/0.25% to 2%/4% weight-to-volume in decane ratio ranges. The lipid containing solution was first placed in an ultra-sound bath for 1 minute to insure homogeneity and was then introduced to the 1 mm diameter Teflon aperture by means of a fine sable hair brush. The resulting lipid plug trapped in the aperture between the two 5 ml volume aqueous solution compartments containing 0.1 M electrolyte spontaneously thins to form a region consisting of a BLM, surrounded by a torus of excess lipid and solvent. Membrane thinning could be stimulated by small electrical potential or mechanical shock in order to speed the process. Observation of BLM formation could be directly accomplished through use of electrical monitoring of transmembrane charge passage or by surface optical reflectivity properties. Pre-treatment of the Teflon support was performed by applying a thin coat of membrane forming solution on both sides of the polymer surface directly around the aperture, allowing the film to air dry. Teflon was cleaned using strong base and chromic acid treatments. Membranes were formed under a direct applied potential ranging from +5 to +50 mV, and were allowed to stabilize for a minimum of 10 minutes before any investigations were performed.

EXAMPLE 2—BLM Investigation and Modification

Phosphatidyl choline was used as the lipid in the following examples. It produces stable BLM readily and has been well characterized by crystal and spectroscopic techniques. A representative summary of the distribution of hydrocarbon residues is listed below for egg derived phosphatidyl choline:

| Hydrocarbon | Percent Composition |
| --- | --- |
| 16.0 | 33.0 |
| 16.1 | 2.1 |
| 18.0 | 15.4 |
| 18.1 | 31.7 |
| 18.2 | 17.8 |
| 20.4 | 4.3 |
| 22.6 | 1.7 |

The phase transition temperature is such that BLM may form at all the prevalent conditions employed in these experiments. Introduction of lipid solution to the Teflon aperture by the brush technique represented the most facile manner in which BLM could be created. Free BLMs as employed in this work are simple to characterize by direct optical and electrical observations. Structural variations such as surface area or presence of unthinned lipid/solvent plugs are thus quickly identified. The one important detriment to use of free membranes is their extreme sensitivity to mechanical or electrical shock. Under the latter conditions the existence of BLM becomes tenuous. One way to achieve membrane integrity is through the use of cholesterol, which can induce the structure to become more dense, and resistant to rupture through shock. Cholesterol is useful for this purpose (assuming a lipid content of 2% w/v) over a range of 0.25% to 4% w/v in solution. Concurrently, cholesterol addition offers a convenient method of altering membrane structure for investigation of electrochemical structural relationships. Cholesterol and phosphatidyl choline can be combined in a maximum molar ratio of C/PC:1/1 in unsonicated solution and still produce apparently homogeneous membranes. A higher sterol content can be obtained (maximum C/PC:2/1) but mixtures must be sonicated for homogeneous dispersion and are susceptible to separations as influenced by lipid fatty acid composition and ambient temperature.

The 2/1 ratio is therefore attainable, but the 1/1 ratio is favoured. Above 20% mole fraction cholesterol, isolated sterol rich zones suddenly become connected forming a lattice network across BLM. Such connected domains may have significant ramifications with respect to ion diffusion control and membrane molecular adsorption properties.

Optical observations of the thinning process of a lipid/solvent plug are dependent on a critical angle of reflection of visible light resulting in the production of interference patterns. The coloured patterns disappear when a BLM forms due to the destructive interference of light reflected from the front and back faces of the membrane since face separation becomes less than 30 nm and phase angles for reflection from the two planes are 180° out of phase. The membrane appears black only when no radiant background illuminates the structure. The loss of colour and subsequent BLM formation may proceed in two steps. An initial dark silver-grey reflectance appears on thinning to a multilayer of approximately 30 nm diameter. Further thinning results in BLM formation and the appearance of a black membrane, the colour being typically referred to as secondary black. The length of time for thinning to occur is a function of solvent viscosity and purity of the lipid/cholesterol components. As chemical decomposition of the latter occurs, membrane thinning velocity is substantially retarded, the observation being useful as a very qualitative judgment of membrane composition.

The BLM may be considered as an aqueous solution based analogue to "soap bubble" chemistry which occurs in the gas phase. A similar series of conditions and restrictions determines BLM formation and stability. The most significant feature revolves around the solubility of the lipid solvent in the aqueous support phase. Should the solvent be soluble in water, then extraction from the membrane becomes a continuous process and not only continually changes BLM character, but may ultimately cause structural failure. This is true for solvent systems such as methanol/chloroform, which should be avoided. Hydrocarbon solvents from octane to hexadecane offer the best characteristics as lipid solvents for BLM formation though octane and nonane are slightly water soluble. A direct correlation between solvent hydrocarbon chain length and membrane hydrocarbon region thickness exists and can be utilized to prepare thick membranes which have greater mechanical stability. Short chain hydrocarbons produce membranes of greatest diameter, while membranes formed from hexadecane are almost solvent free but often contain numerous "lenses" of unthinned lipid/solvent which do not readily coalesce into the torus. Through judicious choice of solvents, membrane hydrocarbon thickness can be altered by a factor as great as 100%. Phospholipids as used in the following examples form aggregates in hydrocarbon solvents. The presence of lipid in the solvent greatly enhances solubility of cholesterol, which presumably packs in an ordered manner within the aggregates. These conglomerates must migrate to the aqueous phase/lipid-solvent plug interface to spread and form monolayers before solvent drainage to the torus can occur. The process is enchanced by:

(1) operating at a higher temperature to increase translational motion (2) sonicating the mixture before use to minimize aggregate size (3) pretreatment of the membrane support surface (Teflon) to deposit dry lipid, which is readily swept across the solvent plug/aqueous interface to form a monolayer when lipid/solvent is introduced to the aperture.

The choice of decane as the solvent in these examples represents the optimum compromise between membrane thickness, viscosity and limitation of lens formation.

The proper pretreatment of the Teflon support is a key factor in determining the stability and lifetime of BLM. The polymer surface around the aperture is painted with the lipid/solvent solution, allowing the solvent to evaporate and leaving a dry residual lipid coating. The success of this process is related to the wettability of the surface which is intimately related to polymer cleaning techniques. Contact angle measurement for lipid/solvent droplets on the polymer represents a quantitative measure of wettability. Coupled with scanning electron microscopy and x-ray photoelectron spectroscopy, such contact angle measures have indicated that Teflon etching with a strong oxidizing medium such as chromic acid will create a physically pitted and rough morphology covered with carbon-oxygen containing species optimizing wettability characteristics.

Stable BLM may be formed from decane solutions containing as little as 0.1% w/v of both cholesterol and lipid, though the 2% ratio appears to represent an optimum concentration for enhancing lipid/solvent plug drainage time and ultimate electrical stability. Regardless of the preceeding ratios, the application of the lipid/solvent to the submerged aperture can directly determine BLM stability. Only a minimal quantity of the hydrocarbon system should be applied since excess solvent adsorbs and wets the polymer surface, eliminating the formation of a torus which supports the membrane. The membrane is instead supported by the surface-adsorbed mixture which places lateral forces on the organized lipid structure by slowly spreading across the Teflon, eventually leading to destabilization.

EXAMPLE 3—Preparation of Stabilized, Supported Membrane

Ordered lipid membranes were interfaced to stable gel substrates, by thin film deposition methods. A lipid-based transducer deposited on a hydrogel, which was physically stabilized on an electrochemical reference electrode, was constructed and tested. A clean glass wafer measuring 1×4×0.1 cm was placed in a vacuum chamber and coated with a 20 nm thickness of Ti/W coating improving adhesion of a further 100 nm Ag metal deposition on to the glass substrate. The wafer was then further processed to prepare a reference electrode surface by, in one case, standing in an aqueous 1 M $FeCl_3$ solution (loosely bound, highly conductive Ag/AgCl), and in another case, by electrolytic deposition accomplished through chloridizing in a 0.1 M HCl solution (compact, relatively non-conductive Ag/AgCl) initiated with a large current transient to prevent nucleation problems and completed at a current density of 5 mA/$cm^2$. Partial encapsulation of the glass wafer with a hydrophobic non-conductive epoxy resin followed so that a reservoir to hold the gel could be formed and homogeneous lipid coating could be optimized by elimination of imperfections which could occur at wafer edges. The epoxy resin was prepared by mixing 100 parts Epon 825 (Shell) and 37 parts Jeffamine D-230 (Texaco) plus 0 to 12% of the hydrophobic thixatrope Silanox (Cabot Corp., Boston, Mass.). The preparation was cured by allowing the coated wafer to stand at ambient room conditions for a period of 12 hours, followed by baking at 60° C. for 3 days.

Acrylamide, N,N'-methylene-bis-acrylamide, N,N,N,N'-tetramethylethylenediamine (TMED) and riboflavin-5'-phosphate (Bio-Rad Laboratories, Mississauga, ON) were prepared as follows for production of a polyacrylamide hydrogel. Monomer solution consisted of 20% w/v total monomer concentration containing 19:1 (w/w) acrylamide/bis-acrylamide in 0.1 M phosphate buffer (pH 7). Riboflavin-5'-phosphate was prepared as a 0.01% (w/v) solution in the phosphate buffer. All solutions were oxygen free and stored under nitrogen. A 0.5 ml volume of monomer, 10 ml TMED and 0.5 ml riboflavin solutions were added successively to a vial purged with nitrogen. A small volume of this reaction mixture was then transferred to the reservoir on the wafer (stored under nitrogen) and polymerization was induced by irradiation for one hour at 254 nm (Lamp Model UVGL-25, Ultraviolet Products, San Garbiel, Calif.). The water was then stored in 0.1 M KCl solution for at least one hour.

A 1:1 weight mixture of egg derived phosphatidyl choline (Avanti Biochemicals, Inc., Birmingham, Ala.) and cholesterol (Sigma Chemical Co., St. Louis, Mo.) as conventionally employed in BLM experiments was prepared in n-hexane, and a small volume was slowly spread on a 0.1 M KCl subphase in a Teflon Langmuir-Blodgett trough. The surface film was compressed by a moving sweep boom until a pressure of at least 30 $mN.m^{-1}$ was attained. The wafer was then dipped repeatedly at a rate of 0.5 cm/min. at fixed pressure (variation 0.1 $mN.n^{-1}$) through the compressed lipid film, first being immersed into the subphase, then withdrawn and finally reimmersed. A small portion of the non-processed clean metal initially deposited on the glass wafer was used as one point of electrical connection to prepare an electrochemical circuit. A Ag/AgCl single junction reference electrode (Orion Research Inc., Cambridge, Mass.), a +25 mV DC power supply and a digital electrometer (Keithlety Model 616, Cleveland, Ohio) completed the circuit for measurement of ion current through the deposited lipid layers. The electrochemical probes phloretin (3-[4-hydroxyphenyl]-1-[2,4,6-trihydroxyphenyl]-1-propanone) and valinomycin (Sigma) were introduced to the trough subphase as concentrated methanolic solutions in the vicinity of the wafer to evaluate transducer operation.

Electrochemically successful BLM casting was readily observed as a 10,000 fold or greater reduction in ion current in the electrical circuit. Final current values had magnitudes on the order of $10^{-9}$–$10^{-10}$ A/cm$^2$, and special electrical shielding with a Faraday cage assembly was employed to reduce electrical interference. Once a stabilized BLM had apparently been deposited on a gel surface, electrochemical probing of the membrane was accomplished by employment of two membrane active organic agents. Valinomycin is an antibiotic (GMW-1111) capable of complexing a cation into a central polar cavity, which is surrounded by a hydrophobic peptide sheath. By virtue of this salient feature of such an antibiotic, it can readily dissolve into nonpolar media, carrying the ion into a hydrophobic zone. This capability has been exploited in the development of neutral carrier electrodes, and results in substantial increases in ion current through BLM by reducing Born energy requirements of ion transport. A transient ion current increase was observed on addition of a local concentrated volume of valinomycin which rapidly dissipates, consistent with the presence of an ion current limiting lipid membrane of undefined structure. A second probe of interest is the dipolar species phloretin. This small organic species (GMW-274) has a large 5.6 D dipole moment which can align against the inherent dipolar field of a BLM. This latter dipolar field is of an orientation which limits transmembrane cation current, so that phloretin acts to increase current. The electrical activity of phloretin is of importance since the dipolar effect is a surface phenomenon and is expected to be significant for only monolayer or bilayer lipid structures.

The electrical activity observed with the probes described above demonstrate that it is possible to deposit lipid monolayers successively onto an ion conductive substrate, creating an organized structure capable of electrochemical response. Using essentially the same techniques, a supported monolayer lipid membrane can be prepared, which acts in the same way. Suitably, for a monolayer, a more hydrophobic substrate is used. The wafer is dipped only one time through the lipid film in the Langmuir-Blodgett trough, to form a monolayer.

EXAMPLE 4—Ammonia Sensing in the Gas Phase

An apparatus as illustrated in FIG. 5 was used. A BLM 3 was formed as described in Example 1 from a 2% lipid, 2% cholesterol solution in n-decane. The Teflon membrane 52 is semi-permeable to permit ammonia gas to pass therethrough, but to prevent passage of liquids. It is used as an interface between the fragile free BLM and the gas sample. Aqueous electrolyte is contained in compartment 50, into which the ammonia dissolves. Polypeptides are incorporated in the BLM, which preferentially complex and transport ammonium ions across the membrane to increase the ion current. Preliminary experiments in a solution cell indicated that, of the tested polypeptide antibiotics (gramicidin, valinomycin and nonactin), nonactin has the greatest selectivity for ammonium ion, relative to potassium and lithium salts used in the electrolyte, as transport ions. The BLM was consequently loaded with nonactin, to equilibrium with a final aqueous solution concentration of $10^{-5}$M, but not to the point of saturation.

From the measurements of ion current passing through the BLM, using reference electrodes on either side of the BLM 3 the concentration of ammonia in the gas phase (partial pressure thereof) could be calculated. The calculations use basic diffusion equations for the diffusion of ammonia through the Teflon membrane into solution, involving diffusion coefficient, BLM area and Teflon membrane thickness as constants and regarding the Teflon membrane operative area as the same as the BLM area. In practice, a calibration curve of ion current through the BLM against ammonia concentration, both as logarithmic values, can be established for this purpose and provided with a given apparatus. Moreover, it was found that readings were essentially unaffected by the presence of chemically similar compounds such as methylamine, ethylamine, hydrazine, cyclohexylamine and octadecylamine. Ammonia concentrations as low as $10^{-6}$M can be thus detected quantitatively.

EXAMPLE 5

A liquid electrochemical cell as diagrammatically illustrated in FIG. 4 was used, to determine antigen concentration in KCl electrolyte. The BLM was prepared from a n-decane mixture of lyophilized phosphatidyl choline and recrystallized cholesterol, as described in Example 1. The electrolyte in both compartments was 0.1M KCl, at pH 7. All experiments were performed at room temperature. The immunochemicals consisted of whole molecule lyophilized whole serum rabbit IgG antiserum (Sigma Chemical Co., St. Louis, Mo.) and lyophilized rabbit IgG immunoglobulin (Sigma), and were both redissolved in electrolyte solution for membrane addition. Membranes were formed under an applied potential of $+5$ to $+50$ mV and their production was monitored by surface optical reflectivity properties. After stabilization the transmembrane current was measured for addition of the various reagents to a lipid-uncontaminated solution compartment. The two antibodies react to form a complex, which deposits on the membrane.

Figure 6:
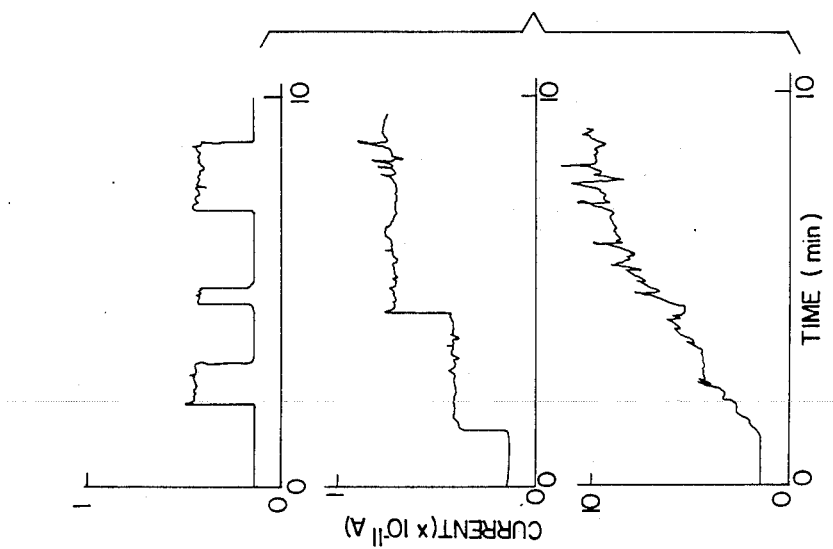
FIG. 6 is three graphs of trans BLM-current against time, for Example 5.

The addition of antiserum and antigen to final concentrations of $10^{-7}$M to $10^{-8}$ M on one side of the BLM produced significant changes in current after incubation periods of between 3 and 30 minutes. FIG. 6 shows typical results which involve either evolution of a series of stepwise or rapid continuous current increases. Signal magnitude and type were associated with reactant concentration, where step rises in current were more commonly observed at lower concentrations. Accordingly, in analytical practice, one can determine concentrations present, as within or outside certain known ranges, by the shape of such curve obtained. Membrane mechanical integrity was greatly influenced during these processes. The presence of inactive antiserum and antigen protein did not influence BLM electrochemistry as demonstrated by the addition of antigen and freshly temperature denatured antiserum (56° C. for 30 min). This chemically-selective membrane is representative of ion current modulation by the formation of pores through a BLM.

EXAMPLE 6

Figure 7:
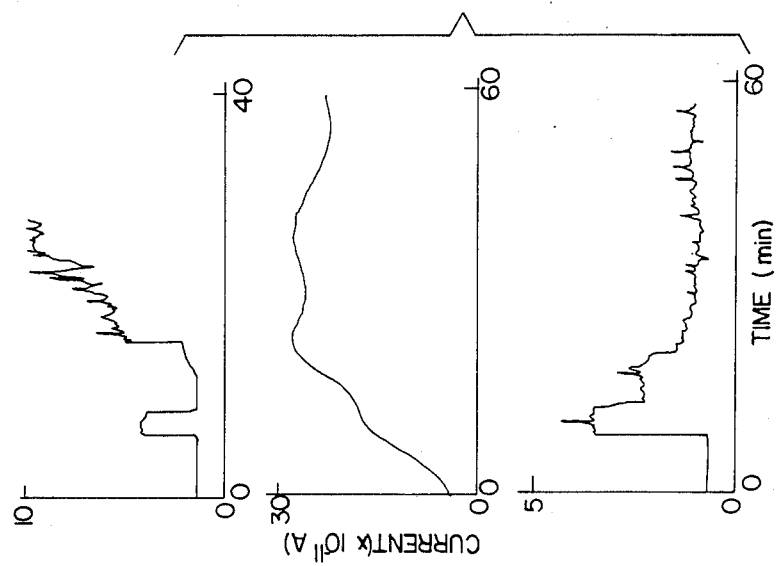

A liquid electrochemical cell employing a BLM as described in Example 5 was used to selectively determine polysaccharide concentration in 0.1 M KCl electrolyte. The glycoreceptor, concanavalin A, and polysaccharides glycogen and dextran (Sigma) were all prepared in electrolyte solution. All experiments were performed at ambient room temperature at pH=7. The antibiotics valinomycin and nonactin (Sigma) were employed to probe receptor action and were prepared as methanolic solutions. Concanavalin A was introduced into one solution compartment to a final concentration of $10^{-5}$ to $10^{-7}$M and polysaccharide was added as a saturated aqueous solution to a final concentration representing 2 percent of the saturation value. Glycoreceptor activity was established by addition of $Ca^{2+}/Mn^{2+}$, to a concentration of $10^{-4}$M, to create binding sites on the concanavalin. For a selective response to ensue, $Mn^{2+}$ and $Ca^{2+}$, concanavalin A and saccharide must be present in the reaction chamber (addition in any order). There is an induction period before the onset of response, which is greater in magnitude if the protein is the last reagent added for reaction. Three distinct types of current-time profile observed in these experiments are summarized in FIG. 7. Thus the polysaccharide concentration level is determined, at least semi-quantitatively, by observing the nature and shape of the curve thus obtained. Experiments to determine the relationship between protein-saccharide complex stability and BLM response indicated that no correlation exists, rather response appeared to be a function of saccharide size. Control of electrochemical response, as distinguished between continuous and step-wise current changes, could be practically chosen by employment of appropriate BLM chemistry and reactant concentration ranges. Step-wise current increases were prevalent for BLM containing little modification by oxidized phosphatidyl choline and steriod products, whereas continuous current changes were commonly observed when the latter products were employed. Step rises in current were never observed in when mono- or di- saccharides were stimulants, though such step rises are commonly observed with large polysaccharides. In further experimentation, the concanavalin A-ions-glycogen system was established as previously described to provide optimized step rises in current. Then valinomycin was incorporated into the membrane by introducing the antibiotic to one solution compartment to a final concentration of $10^{-8}$M. After 30 minutes were allowed to elapse to insure equilibrium, further steps generated by the glycoreceptor complex were substantially increased in magnitude. Identical work substituting nonactin in place of valinomycin confirmed up to 100-fold current increases. These results are documented in FIG. 8, curve A being a current-time graph illustrating the current leap on addition of valinomycin, and curve B being similar but relating to addition of nonactin. The concanavaline A glycoreceptor system represents a selective receptor which operates by dipole potential and by molecular packing modification. It also demonstrates how a receptor complexation signal can be chemically amplified by membrane internal facilitation of conduction by ion carriers and presumably pores.

The concanavalin A appears to alter the dipole at the BLM surface, to increase the trans-membrane current. The antibiotic complexes with the $K^+$ transport ion, to provide it with a non-polar native for assisted movement through the non-polar regions of the BLM as previously described (Born energy reduction). Use is thus made of a combination of two of the transport mechanisms to amplify the ion current signal.

EXAMPLE 7

A liquid electrochemical cell employing a BLM as described in Example 5 was used to study an enzyme-inhibitor interaction. Egg phosphatidyl choline and cholesterol in a 2:1 ratio were used to form the BLM Bovine pancreas trypsin E.C. 3. 4. 21. 4 (Sigma), as aqueous solution of 1 mM phosphate buffer, pH 3.56, was introduced into one solution compartment held at corresponding pH to a final concentration of 0.05 mg/ml. Membrane adsorption was allowed to reach equilibrium by allowing a 15 minute time lapse before the inhibitor phenylmethylsulphonyl fluoride (Sigma) as aqueous solution was introduced to the same solution compartment at excess concentration. Interaction of the BLM with trypsin caused a small increase in permeability, but binding with the inhibitor resulted in current increase, then membrane destabilization and rupture. This is an example of a receptor complex modifying BLM current by gross alterations of intermolecular associations. The measurement is quantitative in that membrane rupture indicates that a certain, predetermined concentration of enzyme has been exceeded.

EXAMPLE 8

A liquid electrochemical cell employing a BLM as described in example 5 was used to study a hormone receptor-hormone interaction. The hormone receptor was prepared as follows: membranes were prepared from coleoptiles and primary leaves (100 g) of maize (*Zea mays* CV. Blizzard) by differential centrifugation between 4000 g and 80,000 g. Auxin-binding proteins were solubilized from the membrane by a non-detergent method and partially purified by ion exchange chromatography. The pooled active fractions were precipitated with ammonium sulphate (80% saturation) and desalted on a 6 cm×1.5 cm column of Sephadex (Pharmacia) G25 to yield 2.4 ml of excluded protein in 50 mM sucrose, 1 mM Mg SO$_4$, 2 mM citrate-acetate, pH 5.5. The active receptor concentration was calculated as about 3 uM by binding assays. The preparation was lyophilized in 100 ul aliquots and stored dry at 4° C. until ready to use. When required, the aliquots were each reconstituted in 100 ul of distilled water and the required volumes were introduced directly into the electrochemical cell electrolyte, as were naphthalene acetic acid (NAA, as methanolic solution), ATP and inactive auxin analogue, benzoic acid. Lipid membranes were prepared as 2% w/v phosphatidyl choline and cholesterol mixtures in n-decane. Experiments were performed in 0.1 M ICCl at pH 5.3, at room temperature. A wide range of experiments probing effects of individual reagents (e.g. NAA, ATP, receptor) indicated that only the receptor preparation produced dramatic results, which were characterized by membrane destabilization within 20 minutes for receptor concentrations greater than $2 \times 10^{-8}$M. Combinations of ATP and receptor solution, or ATP and NAA, or NAA and receptor produced only minor changes in membrane ion flux. However, addition of the three components NAA, receptor and ATP, in any order, resulted in substantial current increases. With benzoic acid in place of NAA there was no response, but an ion flux increase was almost instantly generated by addition of NAA. This receptor system illustrates membrane ion current modulation by a selective interaction which drives ions through an energy intensive pore mechanism.

EXAMPLE 9

A liquid electrochemical cell employing a BLM as described in example 5 was used to study an enzyme-substrate interaction. Membranes were formed from lipid mixtures of 2% W/V ratio of both egg phosphatidyl choline and cholesterol in n-decane. Electrolyte consisted of room temperature 0.1 M KCl adjusted to pH 7. Acetylcholinesterose E.C. 3.1..1.7 (Sigma) was introduced as an aqueous TRIS buffer (pH 7) solution into one electrolyte solution compartment to a final concentration of 0.001 mg/ml. After a period of 10 minutes, during which no substantial ion current changes were noted, acetylcholine (Sigma) as an aqueous solution was added to the same solution compartment to a concentration of $10^{-5}$M. Almost instantly the ion current increased on a relatively continuous basis at these high concentrations of reactants. This represents an example of a selective receptor interaction which modulates ion current by channel formation.

EXAMPLE 10

Figure 9:
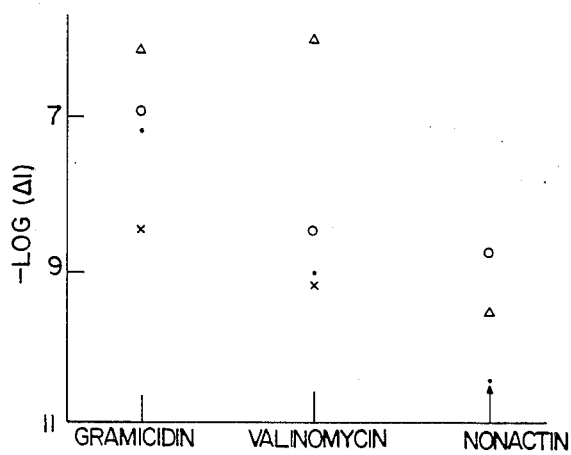
FIGS. 9 and 10 are graphical presentations of results from Example 10.
Figure 10:
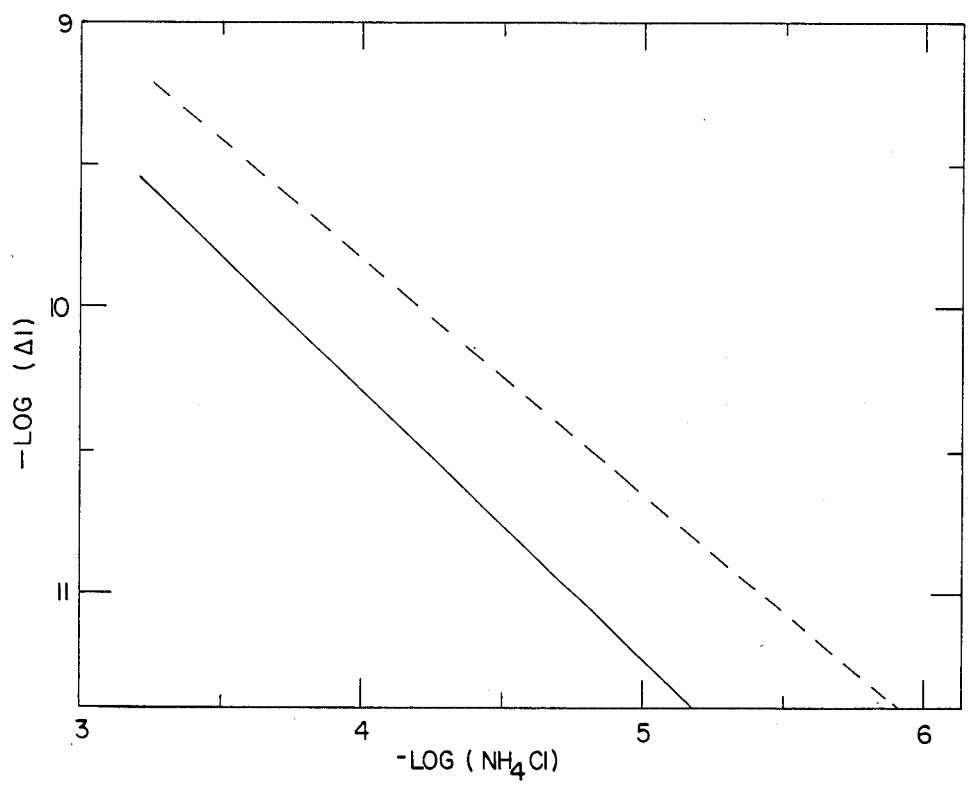

A liquid electrochemical cell employing a BLM as described in example 5 was used to investigate the BLM as an ion-selective electrode. The BLMs were formed from a 2% egg phosphatidyl choline, 2% cholesterol mixture in n-decane. Once stabilized BLM had been formed, ion selectivity could be modified by incorporation of different antibiotics such as gramiciolin, valinomycin and nonactin (Sigma). The change in transmembrane ion current with antibiotic added (as methanolic solution) to one solution compartment to various 0.1M salt solutions was employed as an indicator of ion selectivity. Concentration-response curves for various selective membranes were also determined. FIG. 9 illustrates a comparison of ion currents observed in the presence of different antibiotics at fixed standard concentration as determined by ion selectivity. An example of an ion selective electrode response is shown in FIG. 10. The device was prepared in the standard electrochemical arrangement as described in example 5. One electrolyte compartment containing $10^{-3}$ or $10^{-4}$M LiCl was then adjusted to contain $10^{-5}$ nonactin. Nonactin readily incorporates into BLM and has poor selectivity for Li$^+$, so that only a minimal ion current was present. However, NH4$^+$ ion to concentrations of $10^{-6}$M could be measured selectively when comparing response to Li$^+$ or other organic amines such as ($10^{-2}$ to $10^{-3}$M) methylamine in ionic form. This represents a membrane modified with an antibiotic which transports ions selectively by a pore or carrier mechanism, and results in an ion selective BLM where preferential ion transport due to antibiotic-ion affinity results in ion currents dominated by particular ions.

EXAMPLE 11

A liquid electrochemical cell employing BLMs as described in example 5 was used to investigate ion current control through BLM by manipulation of membrane chemistry for optimization of selective receptor positioning and function. The energy barrier to inorganic (K$^+$) ion conduction through BLMs has been studied as a function of molecular packing and dipolar potential characteristics. Arrhenius energy barrier information (direct measurement of the energy barrier to transmembrane ion current) was derived from temperature dependent electrochemical experiments employing egg phosphatidyl choline (PC) and steroid BLM. A correlation of the barrier magnitude with molecular packing characteristics, obtained by collecting monolayer data from a Langmuir-Blodgett thin-film trough, indicated that BLM ion current was almost completely controlled by molecular density. The sensitivity of energy barrier variation to molecular packing was as great as 100 mV for a 0.01 nm$^2$ adjustment.

The steroids used to control intermolecular interactions in the membrane headgroup zone were 5α-cholesten-3β-ol, (cholesterol), 5α-cholesten-3β,7α-diol, (diol), 5,7-cholestadien-3β-ol, (5,7-diene), 3β-hydroxy-5-cholesten-7-one, (7-one), cholesten-3α,5β,6β-triol, (triol); 5α, 6α-epoxycholestan-3β-ol, (epoxy), and 5α-cholestan-3-one, (3-one) (all from Research Plus Inc., Bayome, N.J.) The egg PC steroid mixture used for BLM formation consisted of 20 mg PC/20 mg steroid in 1 ml of dry n-decane. After BLM stabilization in 0.1 MK Cl at pH7, an infrared heat source was activated and the transmembrane current was measured as a function of temperature. The temperature range investigated was from 21° to 32° C., and was ramped at approximately 0.5° C./min. Similar experimentation was used to study the electrochemical properties of mixtures of cholesterol and oxidized egg PC in an identical weight ratio. The oxidized PC allowed control of the intermolecular interactions in the membrane non-polar zone. The egg PC (Avanti) was dispersed in dry n-decane in a 2% w/v ratio. Oxidation proceeded by irradiating the mixture, contained in a thin-walled glass vial, with intense short wavelength (254 nm) ultraviolet light at ambient room conditions in an air atmosphere. After oxidation had proceeded for a measured period of time, sufficient cholesterol was added to prepare the final BLM-forming mixture. The purity of all lipid components and the degree of oxidation of the PC was monitored quantitatively by a standard capillary gas chromatographic technique employing a transmethylation procedure.

A correlation of electrochemical results with data describing intermolecular interactions was desired. A Langmuir-Blodgett thin-film trough (Lauda Film Balance 1974, Sybron-Brinkman) enclosed in an environmental protection box provided the latter results. The weight ratios and chemistry of the monolayers studied by this device were identical to those used for BLM experimentation, however all solutions were prepared in hexane (using chloroform as a secondary solvent where necessary). Solutions were sonicated briefly and then 100 ul was slowly transferred to the pure water or 0.1 M KCl subphase in the trough. Compression experiments were initiated 10 minutes after spreading of such solutions and consisted of slow compressions in all cases. Tests on the effects of subphase ionic strength and temperature allowed for estimates of corrections necessary for interpretation of results, which were of minor consequence in all cases. The results indicating molecular packing control of ion current indicated a tremendous sensitivity of 100 ml for a 0.01 nm$^2$ alteration. Knowledge of the dipole magnitude of the steriods allows calculation of the monolayer dipolar potential, and implies that transmembrane ion current alterations can be predominantly controlled by intermolecular interactions. The influence of the steroids with respect to the magnitude of the measured Arrhenius barrier was much greater than the oxidized PC, indicating that membrane surface chemistry could play a dominant role in controlling ion current. These experiments demonstrate that a selective receptor designed to control BLM ion current should be located in the surface volume of the membrane and should operate mechanically by substantially perturbing underlying membrane internal order on binding to stimulant. Furthermore, this example demonstrates useful methods of modifying BLM chemistry to adjust the magnitude and position of ion energy barriers to optimize receptor function.

EXAMPLE 12

A liquid electrochemical cell employing BLMs as described in example 5 was used to investiqate amplification of ion current due to dipolar potential changes by altering intermolecular interactions as per example 11. Membranes were formed from 2% w/v ratios of both egg phosphatidyl choline and cholesterol in n-decane. The membrane forming decane mixture was oxidized by irradiation with short wavelength (254 nm) ultraviolet light, and the resulting chemistry was monitored by capillary gas chromatographic techniques. As oxidation increased, the electrochemical ion energy barrier measured from Arrhenius data decreased as per example 11. The use of the dipolar potential reducing agent phloretin (Sigma), introduced to the 0.1 M KCl electrolyte as a methanolic solution to a final concentration of about $10^{-5}$M, caused substantial increases in ion current for all membranes. A significant increase in ion current for a standard fixed phloretin concentration was observed in membranes formed from more oxidized lipids. This example demonstrates that ion current due to a standard potential modification can be increased by using chemical modifications as in example 11.

We claim:
1. A lipid membrane-based device that utilizes transmembrane ion movement for analyzing the concentration of a selected chemical species,
said device comprising a perturbable, ion-permeable, lipid membrane and
an ion conductive support on which is deposited said ion-permeable lipid membrane, said ion-permeable lipid membrane including a complexing agent for selectively interacting with said selected chemical species to increase transmembrane ion movement, and said ion-permeable lipid membrane having an increased transmembrane ion movement when perturbed.

2. The supported, membrane-based device of claim 1, wherein said ion conductive support is a stable gel substrate.

3. The supported, membrane-based device of claim 1, wherein said ion conductive support is a hydrogel.

4. The supported, membrane-based device of claim 3, wherein said hydrogel is physically stabilized on an electrochemical reference electrode.

5. The supported, membrane-based device of claim 4, wherein said hydrogel is a polyacrylamide hydrogel.

6. The supported, membrane-based device of claim 1, wherein said lipid membrane is a bilayer lipid membrane.

7. The supported, membrane-based device of claim 1, wherein said lipid membrane is a monolayer lipid membrane.

8. The supported, membrane-based device of claim 1, wherein said complexing agent is a receptor selective for an organic compound.

9. The supported, membrane-based device of claim 8, wherein said receptor is a natural product.

10. The supported, membrane-based device of claim 8, wherein said receptor is chemically bound in the membrane.

11. The supported, membrane-based device of claim 1, wherein said complexing agent is selective for an inorganic ion.

12. A gas-sensor electrochemical cell comprising
(a) a gas-permeable membrane permeable to an inorganic ion-forming gas, and
(b) a perturbable, ion-permeable lipid membrane including a complexing agent for selectively interacting with a selected inorganic ion formed by dissolution of said inorganic ion-forming gas in an aqueous electrolytic solution,
said gas-permeable membrane being separated from said ion-permeable lipid membrane by the lipid membrane-contacting, aqueous electrolytic solution.

13. The gas-sensor electrochemical cell of claim 12, wherein said complexing agent is a polypeptide.

14. The gas-sensor electrochemical cell of claim 13, wherein said polypeptide is an antibiotic selected from the group consisting of gramicidin, valinomycin and nonactin.

15. The gas-sensor electrochemical cell of claim 13, wherein said polypeptide is nonactin.

16. The gas-sensor electrochemical cell of claim 12, wherein said gas-permeable membrane is a polytetrafluoroethylene membrane.

17. The gas-sensor electrochemical cell of claim 12, wherein said modified membrane is a bilayer lipid membrane.

18. The gas-sensor electrochemical cell of claim 12, wherein said modified membrane is a monolayer lipid membrane.

* * * * *